United States Patent [19]

Baughman et al.

[11] Patent Number: 5,191,786
[45] Date of Patent: Mar. 9, 1993

[54] METHOD FOR DETECTING THE PRESENCE AND CONCENTRATION OF RELATIVELY LOW MOLECULAR WEIGHT COMPONENTS IN A LIQUID

[75] Inventors: Ernest H. Baughman, Naperville; John R. Winston, Bolingbrook; Kenneth W. Andresen, Glen Ellyn, all of Ill.

[73] Assignee: Amoco Corporation, Chicago, Ill.

[21] Appl. No.: 722,958

[22] Filed: Jun. 28, 1991

[51] Int. Cl.[5] .............................................. G01N 7/16
[52] U.S. Cl. .................................... 73/64.45; 73/19.1
[58] Field of Search ................. 73/64.45, 29.01, 29.03, 73/19.1

[56] References Cited

U.S. PATENT DOCUMENTS 2,811,851 11/1957 Jacobs ................................. 73/64.45
2,847,852 8/1958 Rhodes et al. ...................... 73/64.45
3,491,585 1/1970 Hass ............................... 73/29.01 X

FOREIGN PATENT DOCUMENTS 169049 10/1983 Japan ................................. 73/64.45
54426 3/1986 Japan ................................. 73/64.45
1227991 4/1986 U.S.S.R. ............................ 73/64.45

Primary Examiner—Hezron E. Williams
Assistant Examiner—Joseph W. Roskos
Attorney, Agent, or Firm—Ekkehard Schoettle; Richard A. Kretchmer; Frank J. Sroka

[57] ABSTRACT

Disclosed is a method for determining the concentration of relatively low molecular weight target components in a liquid. The method involves commingling the liquid with a diluent to form a liquid-diluent mixture, stripping the target components from the liquid-diluent mixture, and passing the stripped target components to a detection zone wherein the concentration of each target component is determined absent the separate analysis for each component.

11 Claims, 6 Drawing Sheets

REID VAPOR PRESSURE (RVP)

METHOD FOR DETECTING THE PRESENCE AND CONCENTRATION OF RELATIVELY LOW MOLECULAR WEIGHT COMPONENTS IN A LIQUID

BACKGROUND OF THE INVENTION

Broadly, this invention relates to an apparatus and method for detecting the presence of certain relatively low molecular weight target components in a liquid. In one aspect, this invention relates to an apparatus and method for detecting the presence and concentration of relatively low molecular weight components in liquid hydrocarbons. In another aspect, this invention relates to an apparatus and method for determining the Reid Vapor Pressure (RVP) of a liquid hydrocarbon. In a more detailed aspect, this invention relates to an improved method and apparatus for determining, separately or cumulatively, the concentration of propane, butane and pentane components in crude oil.

In recent years the public has become increasingly concerned about excess ozone formation. While federal regulations aimed at limiting vehicle emissions already exist, public concern has prompted the consideration of even lower limits for allowable gasoline vapor pressure in areas having poor air quality. Lower vapor pressure gasoline emits less hydrocarbons and is therefore less likely to contribute to ozone formation. Gasoline's vapor pressure can be lowered by reducing the concentration of low molecular weight components in the gasoline.

Propane, butane and pentane are the most common low molecular weight components of gasoline. The amount of these "light end" components which must be removed by oil refiners depends on the concentration of light ends in crude supplied to refineries. Crude containing excessive concentrations of light ends is undesirable because refining costs to produce low vapor pressure gasoline are higher when such crude is used. Besides higher refining costs, refiners who pay crude oil prices for light ends contained in crude oil may incur changes for propane, butane and pentane that are significantly higher than the market value of these components.

Crude oil producers and pipeline operators are also interested in knowing the concentration of light components in crude. Producers separate light components from crude before selling it to a carrier. Efficient control of the separation process requires accurate on-line analysis of the RVP of crude oil. Pipeline operators strive to maintain the concentration of light ends in crude at levels low enough to be acceptable to refiners. It is important that carriers prevent crude with excessive concentrations of light ends from entering pipeline systems.

The determination of the concentration of light end components in hydrocarbons is necessary for efficient process control and for accurate custody transfer pricing. To be useful for process control, an apparatus and method for determining the concentration of light ends in liquid hydrocarbons must be adapted to field environments and should be able to generate on-line results. To be useful for custody transfer, such apparatus and method must be suitable for transport to and operation at multiple field locations. Prior to this invention, no such apparatus or method has been available which meets these requirements.

At present, apparatus and methods for determining concentrations of light ends in hydrocarbons include various gas stripping techniques in combination with gas chromatographs or pressure analyzers. U.S. Pat. No. 3,150,516 (Linnenbom et al.) discloses, for example, a system for extracting dissolved gases from a liquid sample and subsequently analyzing the extracted gases using a gas chromatograph. While such instrumentation may be operable for on-line analysis, it is primarily intended for laboratory use. Further, extraction and chromatography typically take 10-20 minutes per sample. The '516 system is clearly unsuitable for remote field applications where portability and durability are critical for utility.

U.S. Pat. No. 3,446,077 (Sanford et al.) discloses, for example, a sampling system which is capable of providing vapor samples from liquid streams. The '077 system does not encompass gas analysis. Further, the apparatus for extracting gas from a liquid comprises a stripping column wherein extraction occurs by means of precisely maintained pressure and flow conditions.

Commercially available Reid Vapor Pressure analyzers include the Model No. 44770 Reid Monitor, manufactured by Precision Scientific of Chicago, Ill. This device is capable of measuring the RVP of distillate fuels, but not crudes, in accordance with ASTM procedures. RVP measurements are made under conditions of constant temperature and carefully controlled vapor to liquid ratios using an absolute pressure bellows and two pneumatic transmitters.

Another commercially available device for measuring the absolute vapor pressure of hydrocarbon compounds, including crude oil and distillate fuels, is the Precision Scientific Model 41351 Absolute Vapor Pressure Monitor. This device continuously measures vapor pressure under conditions of constant temperature and precisely controlled pressure drop across a venturi-type ejector system. It may be calibrated to measure RVP for certain hydrocarbon compounds.

Prior art methods and apparatus for vapor pressure and light ends analysis of liquid hydrocarbons are deficient because they are large, complex devices which require gas chromatographs or other sensitive equipment which tends to be fragile and not readily suited for field applications. Further, prior art methods and apparatus cannot be readily transported to remote locations. Still further, prior art methods are relatively time consuming. For instance, full analysis of a hydrocarbon compound may take 10-20 minutes. Poor response time reduces the effectiveness of prior art methods for on-line applications. Another shortcoming of the prior art is the inability to analyze for light ends in crude oil. Yet another shortcoming is the inability to distinguish between different light end components commonly found in crude oil.

It should also be pointed out that different varieties of crudes having, for instance, different viscosities, gravities, sulfur contents, etc., present different analytical problems. For instance, if a stripping technique is used, different crudes are going to respond differently to the same stripping gas being contacted at the same conditions and in the same amounts, i.e., temperature, pressure, and flow rate.

To illustrate the need for field-ready devices, particularly devices which are portable, it is useful to consider methods commonly used at present for monitoring the quality of crude oil at an inlet point of a pipeline or the loading end of a vehicular transport system. Typically, crude oil is collected in tank batteries servicing local production operations. Prior to reaching custody transfer tanks, certain impurities, including light ends, are removed from the crude. In order to minimize operating costs, producers generally remove only the amount of impurities necessary to meet safety and crude oil quality requirements of regulatory agencies and transport operators.

Very often, crude oil producers establish area offices whose personnel are responsible for the production of crude in oil fields covering many acres. Such area offices are responsible for the operation of various, sometimes numerous, tank batteries scattered throughout their territory. Production economics limit not only the level of staffing for oil fields, but also the quantity and cost of equipment, such as analytical devices for monitoring crude oil quality at custody transfer points. Typically such analysis equipment is available only at a central laboratory located at and operated by the area office. Staffing and equipment limitations prevent close monitoring of crude oil. Transportation operators must contend with similar limitations.

Problems and inefficiencies with present crude analysis methods are made clear in the following example. When an oil producer completely fills a custody transfer tank and desires to sell or otherwise provide such crude oil to the associated transport operator, the quality of the crude oil becomes a matter of interest to both parties: the transporter because he does not want to accept delivery of substandard crude oil, and the producer because he wants to confirm that tendered crude oil either does or does not meet specifications, such as RVP requirements. When a transporter is asked to take delivery of crude, it is common practice to obtain samples of the tendered crude oil for analysis. The crude storage tank is typically sealed while the samples are carried to a laboratory for analysis. If analysis indicates acceptable crude oil quality, the transporter must return to the tank, check then break the seal, and initiate custody transfer. It is not unusual for this procedure to take 24-48 hours. If analysis indicates unacceptable crude oil quality, such as an excessively high RVP, the problem is communicated to the producer, corrective action is taken, and the analysis process is repeated, including inherent inefficiencies in obtaining and transporting samples, and taking custody of the crude oil. Meanwhile, continuing production can be delayed or impeded because tankage is tied up.

While the oil industry has tolerated and adjusted to such problems and inefficiencies, there has long been a need for improved apparatus and methods for determining the concentration of light ends in hydrocarbon liquids. Further illustration of this long felt but unmet need exists with respect to custody transfer pricing, refining and gas separation activities.

The present invention provides for a relatively simple method and apparatus for determining the concentration of target components in a liquid which can be carried out relatively quickly in the field regardless of the type of liquid analyzed. The present invention dispenses with the use of fragile columns as employed in gas chromatographic techniques.

SUMMARY OF THE INVENTION

In a broad embodiment, the present invention provides for a method for measuring the concentration of relatively low molecular weight target components present in a liquid. The method is carried out by obtaining a sample of the liquid having a predetermined volume, and commingling the sample with an excess of a diluent to form a sample-diluent mixture. The sample-diluent mixture is then passed to a stripping zone wherein the target components are stripped from the mixture at a predetermined rate at predetermined conditions. The stripped target components are then passed to a detection zone where a signal is generated responsive to the quantity of each target constituent. A chemometric model is then used to correlate the signal to the concentration of the target constituent thereby determining the concentration of the target constituent.

DETAILED DESCRIPTION OF THE INVENTION

Figure 1:
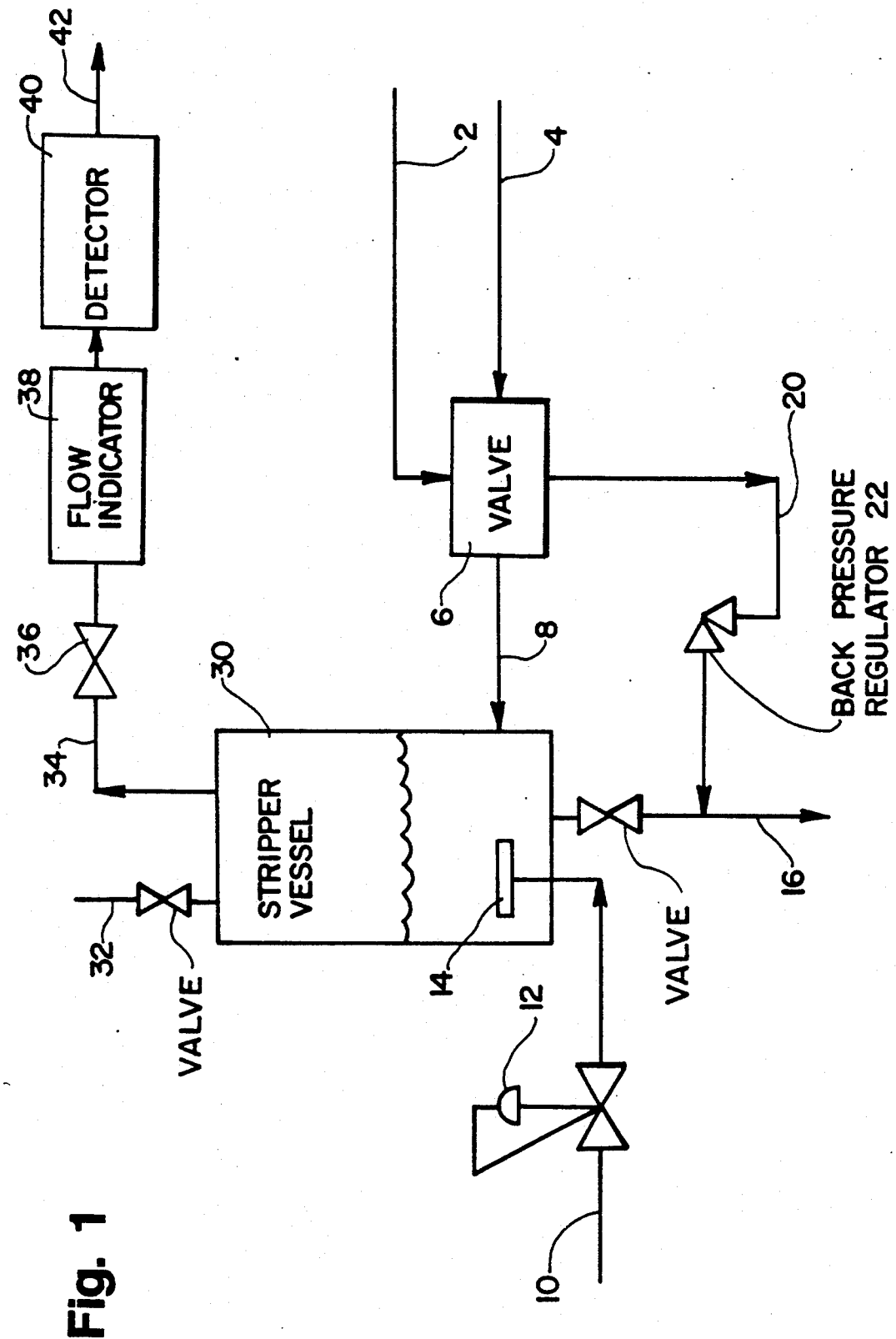
FIG. 1 shows a simplified flow diagram of apparatus, constructed in accordance with the present invention, for detecting the presence and concentration of low molecular weight components in liquid hydrocarbons.

In connection with the present invention, the term "target components" encompasses one or more target components contained in a liquid sample wherein the target components have a molecular weight that is relatively lower than the remainder of the sample. Liquid samples to be analyzed in accordance with the present invention are acquired, for example, from high pressure crude carrier lines, carrier vehicles or tankage. In order to ensure that samples contain representative amounts of target components where the target components are relatively low molecular weight components, it is important that sampling be performed in a manner such that the liquid samples are maintained at a pressure at least as high as the normal system operating pressure. Thus, if the sample is a crude oil the target component could be butane, or butane together with pentane and propane, etc. The upper value of sampling pressures where the sample is a crude oil is limited by crude production, transportation and sampling equipment design ratings. In accordance with the present invention, it is not required that the measuring apparatus be in direct communication with the liquid to be sampled. For instance, portable sampling devices such as a high pressure syringe may be used to extract the sample at the sampling point and deliver it to the measuring apparatus of the present invention.

In accordance with the present invention, a predetermined volume of the liquid sample is commingled with an excess of a diluent. The excess of diluent is required so that in effect the stripping rate of target components at predetermined stripping conditions, i.e., stripping gas flow rate, temperature and pressure is not related to or dependent upon the composition of the liquid sample.

The excess of diluent serves to "normalize" samples such that, for instance, butane would be stripped from a heavy crude sample at the same rate as it would be from a relatively lighter crude sample. At the same conditions, it is known that light components can be stripped at a greater rate from a crude possessing a relatively low viscosity and/or high API gravity than from a crude possessing a relatively high viscosity and/or low API gravity. When a diluent is added to the sample in accordance with the present invention, the disparities in stripping rates are eliminated. Generally, an adequate excess would range from about 0.5 to about 150 volumes of diluent per volume of sample. Preferably, the range is about 20 to about 100, and most preferably about 30 to about 50 volumes of diluent per volume of sample. Generally, as the ratio of diluent to sample is increased, the method of the invention achieves more reproducible measurements.

In accordance with the present invention, the diluent must be a liquid at the stripper conditions and have a low vapor pressure at the stripping conditions. It should also have a relatively low freezing point. Additionally, the liquid sample should be soluble in the diluent. The diluent may comprise a variety of hydrocarbon liquids such as ethyl benzene, cumene and mineral spirits. Cumene is a preferred diluent.

The present invention can also contain means for maintaining sample temperature within an acceptable range during analysis. In applications involving direct exposure to environments of extreme heat or cold, it is desirable that samples be prevented from freezing or overheating. In order to enhance long term reliability of the device, sample temperature should be maintained within an acceptable, repeatable range; about 30° F. to about 120° F. is preferred.

Subsequent to the preparation of the sample-diluent mixture, the mixture is passed to a stripping zone.

Stripping gas is passed to the stripping zone which can be provided from an outside, pressurized source. Stripping gas must be chemically inert with respect to the diluent and/or liquid samples being analyzed. Depending on the type of downstream detection zone employed, air, nitrogen or other inert gases can be used as stripping gases. Aside from constraints imposed by the type of detection zone employed, selection of the stripping gas may be based on availability and convenience. The stripping gas serves to strip the target components from the sample-diluent mixture as described in greater detail below. It is critical that the flow of stripping gas be maintained at a substantially constant rate at the same predetermined conditions, i.e., temperature and pressure, so that target components are passed to the detection zone at a controlled, repeatable rate.

Within the stripping zone, the target components are volatilized and stripped from the sample-diluent mixture. Stripping conditions such as stripping gas flow rate, temperature and pressure can be readily prescribed by those skilled in the art to carry out the desired stripping of the target components. Preferred stripping conditions include a temperature of about 70° F. to about 120° F. and a pressure of about 0 to about 60 psig. Means communicating between the stripping zone and a detection zone are provided, through which volatilized target components are carried by stripping gas. The stripping zone can also be equipped with means for venting and draining the stripping zone. The stripping zone may contain internal contact surfaces known to those skilled in the art (e.g., plates, rings, etc.), however, such surfaces are not essential to the invention.

Target components are carried to a detection zone which is provided with detection means suitable to detect target components, e.g., light end hydrocarbons. As mentioned above, it is important that target components be passed to the detection zone at a controlled, repeatable flow rate. It is possible to determine not only the overall concentration of target components in the sample, but also to determine the amount of each individual component present in the sample. The tendency for lighter weight components to volatilize before heavier components makes this type of analysis possible.

The availability of high-speed, high-powered rugged and inexpensive electronic data processing means makes this type of analysis practical for use outside of laboratory environments.

By applying recently developed but well known chemometrics principles and models it is possible to derive prediction equations for the concentration of target components in samples even though the components are not resolved in the classical gas chromatographic sense. A training set comprising a number of different samples having known properties is analyzed using the invention to generate detector output data which is characteristic of the particular properties of each training set sample. Training set samples are formulated to be representative of, and span the entire range of, properties expected to be encountered in actual samples having unknown properties. Beyond this, the number of known samples in the training set is not critical, although the larger the training set, the more robust will be the resulting prediction equation. Using a regression analysis program, such as partial least squares, training set sample properties and detector output are correlated to derive a prediction equation useful in analyzing actual samples. In effect, the detector's response versus time is calibrated. Thus, detector output with respect to analysis of liquids such as hydrocarbon samples containing low molecular weight components can be used to accurately predict the quantity of each such component without directly analyzing the composition of the samples.

It is understood that the present invention in its broadest aspect pertains to the measuring of target components present in a liquid. The following discussion for illustrative purposes only, is specific to hydrocarbon liquids containing light gases such as propane, butane and pentane. With respect to detection zones, a variety of hydrocarbon detection devices which employ an equally varied range of detection methods may be suitable for use in this invention. It is preferred that any hydrocarbon detector used herein have fast response time. One example of a suitable detector is the Model 4388 Electrochemical Sensor/Transmitter, manufactured by Enterra Instrumentation Technologies of Exton, Pa. Those skilled in the field of combustion gas analysis will appreciate that stripper gas should comprise air when such a detection device is used in the invention. Another example of a suitable detector is the Model IR-703 Infrared Analyzer, manufactured by Infrared Industries, Inc., of Santa Barbara, Calif. Nitrogen, argon or air may be used for stripping when this type of detection device is used in the invention. Other suitable detection devices are available and known to those skilled in the art.

In operation, the detector responds to hydrocarbon vapors generated in and transported from the stripping zone to the detection zone. As mentioned above, detector output can be used to determine not only the overall amount of light ends in the sample, but also the concentration of individual light end components. For example, because the partial vapor pressure of propane is higher than that of butane, which is higher than that of pentane, the first vapor generated during stripping of crude oil samples will be propane enriched. In other words, the propane component is stripped rapidly from crude oil samples relative to butane and pentane stripping rates. Further, the butane component is stripped rapidly relative to the pentane stripping rate, but slowly compared to the propane stripping rates.

As mentioned above, the apparatus and method of the present invention can also be used to determine the Reid Vapor Pressure of a mixture of hydrocarbons. Reid Vapor Pressure is defined as the equilibrium vapor pressure of a hydrocarbon liquid at 100° C.

The accompanying drawings, which are incorporated in, and constitute a part of, this specification, illustrate one embodiment of the invention, and together with the description serve to explain the principles of the invention.

While this invention is susceptible of embodiment in many forms, there is shown in FIG. 1 a specific embodiment with the understanding that the present disclosure is not intended to limit the invention to the embodiment illustrated.

With reference to FIG. 1, liquid hydrocarbon samples are introduced into the invention through sample supply line 2 flowing therethrough to valve 6. In the preferred embodiment of the invention, valve 6 comprises a commercially available six-way valve, such as Model No. SS 43Y6 FS2, manufactured by Whitey Company of Highland Heights, Ohio. Diluent is provided to valve 6 through diluent supply line 4. Samples and diluent are passed into stripper vessel 30 through stripper vessel inlet line 8. Valve 6 communicates with drain line 16 through valve drain line 20 and back pressure regulator 22.

Figure 2A:
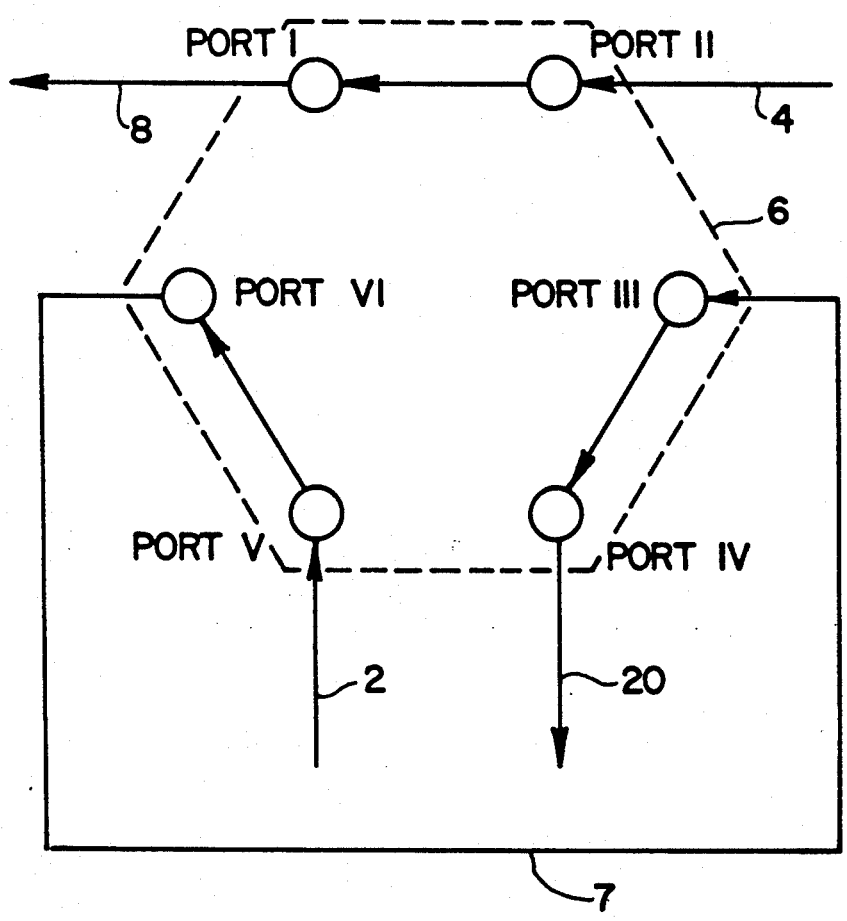
FIGS. 2a and 2b are illustrative schematic diagrams of valve means which can be an element of the present invention.
Figure 2B:
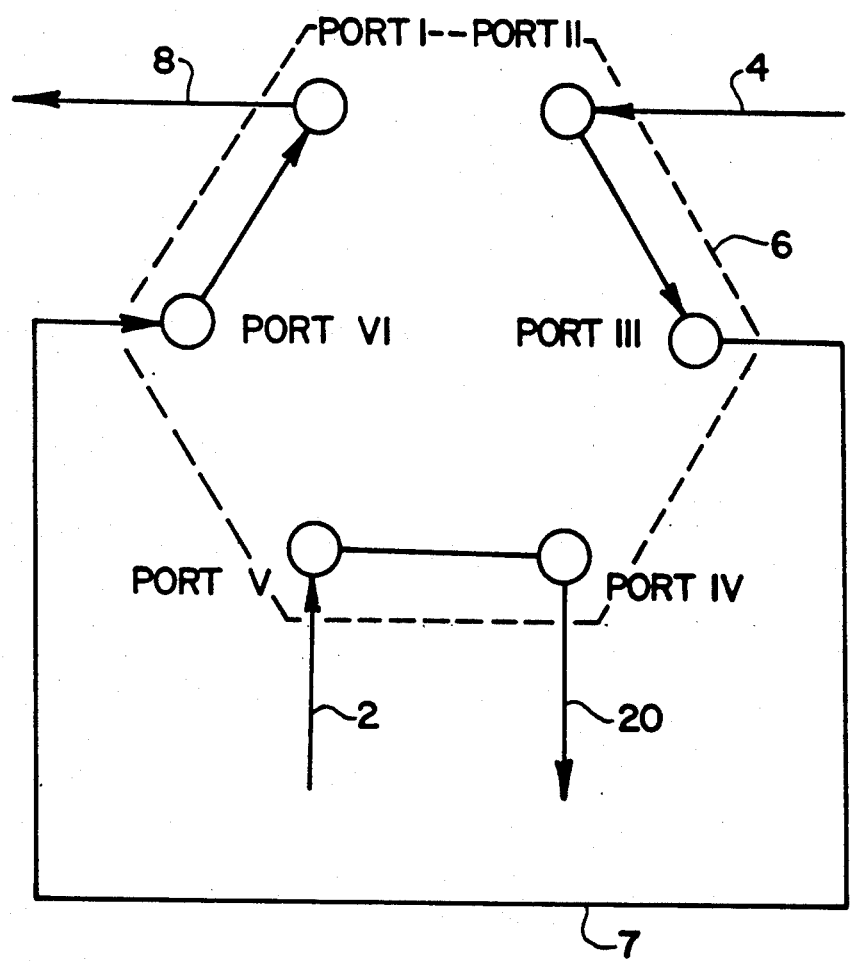

The operation of valve 6 can be understood by referring to FIGS. 2a and 2b. Valve 6 is a six-port valve having three operating positions, referred to herein as Positions One, Two and Three, each position being described in greater detail below. For reference purposes, the ports are numbered I through VI. Metering loop 7, which has a known volume, is a small diameter tube which communicates between port III and port VI.

In Position One, flow through all ports is blocked.

Sample metering occurs in Position Two, which is shown schematically in FIG. 2a. In Position Two, sample liquid provided through sample supply line 2 enters valve 6 through port V, flows from port V to port VI, from port VI through metering loop 7, reenters valve 6 through port III, continues from port III to port IV and hence to valve drain line 20. Further, in Position Two, any diluent provided to valve 6 through diluent supply line 4 enters valve 6 through port II, flows from port II to port I and hence to stripper vessel 30 through stripper vessel inlet line 8.

Injection of metered samples into stripper vessel 30 occurs in Position Three, which is shown schematically in FIG. 2b. In Position Three, diluent enters valve 6 through port II, flows from port II to port III, from port III through metering loop 7, reenters valve 6 through port VI, continues from port VI to port I and hence to stripper vessel inlet line 8. In Position Three, flowing diluent carries before it into stripper vessel 30 any metered sample residing in meter loop 7. Further, in Position Three, any sample provided to valve 6 through sample supply line 2 enters valve 6 through port V, flows from port V to port IV and hence to valve drain line 20.

In the operation of the invention, valve 6, stripper vessel 30 and associated supply, drain and flow lines are maintained at a pressure sufficient to prevent spontaneous volatilization of low molecular weight components from liquid hydrocarbon samples. First, with valve 6 in Position Two, diluent is provided to stripper vessel 30, and sample fluid is metered into metering loop 7. Next, while sample fluid is flowing through metering loop 7, valve 6 is switched to Position One, the fully closed position. Next, valve 6 is switched to Position Three and left in this position until all sample material has reached stripper vessel 30. Finally, while diluent is flowing through metering loop 7 and has carried before it into stripper vessel 30 all metered sample fluid, valve 6 is switched back to Position One. In this way, known volumes of sample are introduced into stripper vessel 30 under pressure.

Referring again to FIG. 1, stripper vessel 30 is a vapor tight container constructed of such materials and in such manner as to permit it to maintain its integrity through sustained use in the service of the invention. More particularly, the material of construction of stripper vessel 30 may be, for example, carbon steel or stainless steel, and stripper vessel 30 must be able to contain a pressure of at least 40 psig at temperatures ranging from −30° F. to 120° F.

Stripper vessel inlet line 8 enters stripper vessel 30 through the bottom or side wall. Preferably, the point of entry is positioned below the liquid/vapor interface when volatilization of target components is taking place inside stripper vessel 30. Diluent and metered samples are supplied to stripper vessel 30 through valve 6 and stripper vessel inlet line 8 as described above. Pressurized stripper gas is provided to stripper vessel 30 through carrier gas inlet line 10. The pressure of stripper gas is maintained at the operating pressure of stripper vessel 30 by means of stripper gas pressure regulator 12. In addition to carrying target components from stripper vessel 30 to the detection zone, stripper gas promotes volatilization and mixing of sample material with diluent of target components present in the sample-diluent mixture present within stripper vessel 30. In order to optimize stripping, it is preferable that stripper gas inlet line 10 extend into the bottom of stripper vessel 30, and that frit 14 be placed on stripper gas inlet line 10 so that carrier gas entering stripper vessel 30 must pass through frit 14 having a nominal size ranging from 2 to 20 microns. Frit 14 is effective to break up a stream of gas into many small bubbles.

Stripper gas carries volatilized target components from stripper vessel 30 through outlet line 34 to detector 40. Flow through outlet line 34 is controlled by flow controller 36. It is critical that flow through outlet line 34 be maintained at a substantially constant rate. Such flow rate is indicated by flow indicator 38. After passing through detector 40, carrier gas and volatilized target components are vented through exhaust line 42.

Stripper vessel 30 is provided with stripper vessel vent 32 and drain line 16 for use in releasing vapors and/or liquids accumulated in stripper vessel 30.

EXAMPLE 1

The present example serves to demonstrate the efficacy of the present invention in connection with determining the butane and pentane content of a crude sample.

Specifically, several calibrating samples were prepared by taking a crude oil and stripping the light ends, $C_2$–$C_5$, therefrom. Subsequently, butane and pentane were added to five samples in accordance with the following weight percentages.

| Sample Number | Percentage by Weight | |
|---|---|---|
| | Butane | Pentane |
| 1 | 5 | 1 |
| 2 | 4 | 4 |
| 3 | 4 | 2 |
| 4 | 3 | 4 |
| 5 | 1 | 5 |

Figure 3:
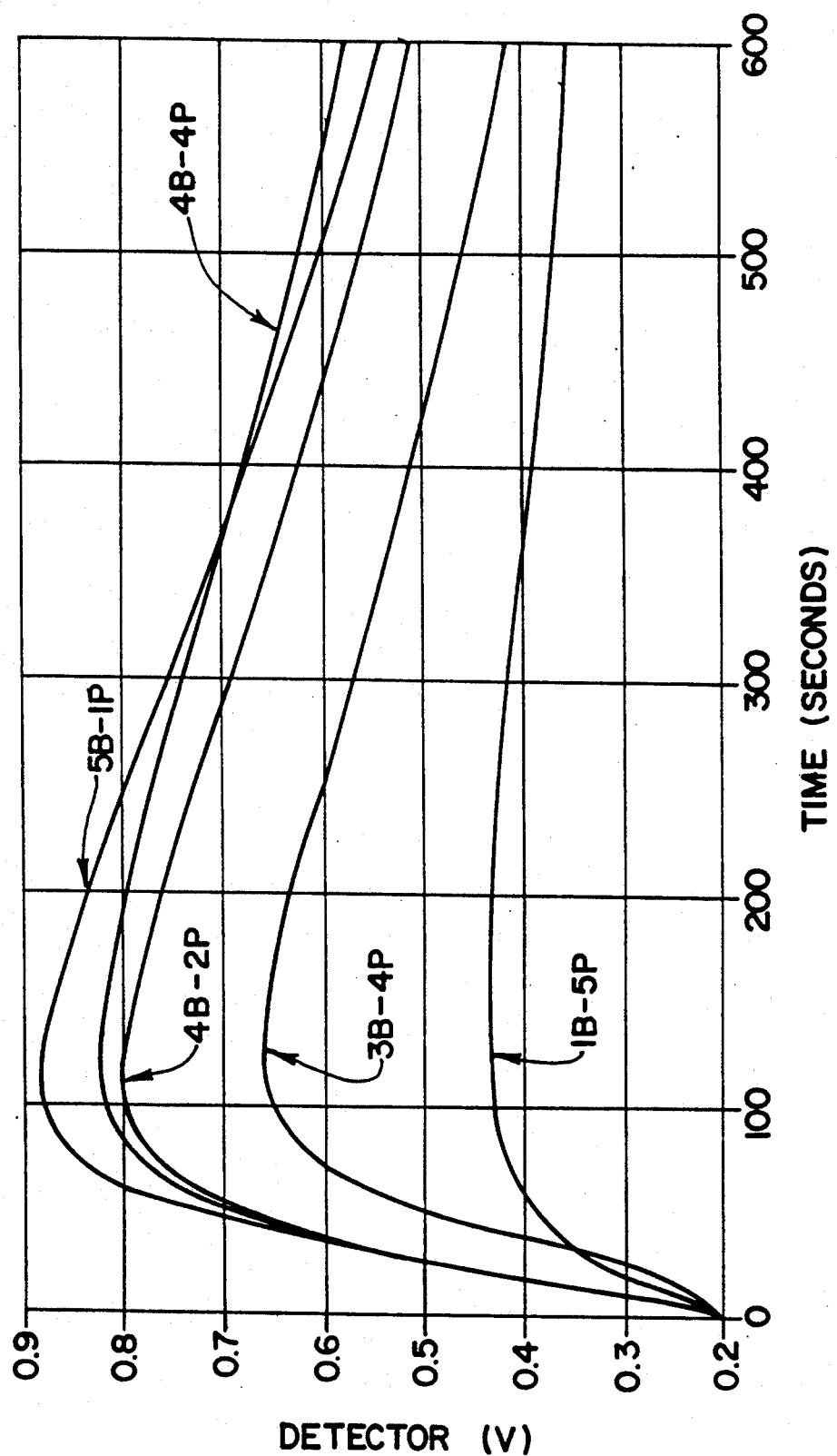
FIG. 3 is an illustrative graphic representation of detector output of total amounts of low molecular weight components in five different hydrocarbon samples analyzed in accordance with the present invention.

The apparatus and method of the invention were employed to generate detector output versus time response curves for each sample. Specifically, in each case a 20 mL sample was diluted with 20 mL of ethylbenzene diluent. The stripping step was carried out by passing 1.5 SCFH of air at room temperature through a cylindrical stripping zone having a 2-inch nominal diameter and height of 4½ inches. The detector used in the present example was a Model 4388 Electrochemical Sensor/Transmitter by Enterra Instrumentation. These curves appear in FIG. 3. A comparison of the curves in FIG. 3 shows the difference in detector response to butane (referred to as "B" in FIG. 3) and pentane (referred to as "P" in FIG. 3) in crude oil. This type of detector output, together with known sample properties, would be suitable for inclusion in a chemometrics training set, as described above, and suitable for calibrating an apparatus to be used in accordance with the present invention. In accordance with the present invention, it is generally preferred to use a greater volume ratio of diluent to sample.

EXAMPLE 2

The apparatus and method of the present invention was employed in the field at ambient temperature and pressure to determine the content of butane and pentane in a wide variety of crude samples from Southwestern Wyoming and Northeastern Utah having differing viscosities, gravities, sulfur contents, etc.

The following table sets out the location source of each crude and the temperature at which the analysis in accordance with the present invention was carried out.

| Sample | Source Location | Temp.. °K. |
|---|---|---|
| 1 | Clear Creek | 279 |
| 2 | East Painter | 289 |
| 3 | Painter Central | 284 |
| 4 | Carter Creek | 282 |
| 5 | Whitney Canyon | 281 |
| 6 | Ryckman | 284 |
| 7 | Glasscook | 273 |
| 8 | Chicken Creek | 277 |
| 9 | West Anschutz | 285 |
| 10 | Pine View Station | 287 |
| 11 | Pine View 3-2 | 298 |
| 12 | Bing 2-1 | 297 |
| 13 | Exxon | 279 |
| 14 | Kevin | 288 |
| 15 | West Anschutz | 291 |
| 16 | Wahsatch | 293 |

The invention results were subsequently compared with a laboratory gas chromatographic analysis of such sample.

In the present example, each sample had a volume of 1.2 mL and was commingled with a diluent volume of 40 mL of cumene. More specifically, a high pressure syringe containing the 1.2 mL sample and 20 mL cumene was used to pass the sample to the stripping column which contained 20 mL cumene. The stripping gas was air and was passed to the stripping column at 1.5 SCFH. The same stripper described in Example 1 was used in the present example. The detector described in Example 1 was employed in the present example to obtain response versus time data at 300 points in time for each sample, where the target components were propane, butane, and pentane. Data processing means, a Toshiba laptop computer Model 1600, was used to solve for the constants in the following equations using the results obtained for 14 of the above 16 samples. Specifically, data from Samples 4 and 16 was not used to generate the correlation.

$$\% \text{ Propane} = \left(\frac{1}{T-A}\right)(a_o + a_1V_1 + a_2V_2 \ldots a_nV_n)$$

$$\% \text{ Butane} = \left(\frac{1}{T-A}\right)(b_o + b_1V_1 + b_2V_2 \ldots b_nV_n)$$

$$\% \text{ Pentane} = \left(\frac{1}{T-A}\right)(c_o + c_1V_1 + c_2V_2 \ldots c_nV_n)$$

where:
T is stripper temperature °K.
A is a temperature correction constant
$a_n$, $b_n$, $c_n$ are constants
n is No. of data points, e.g., typically 300
$V_n$ is a voltage or other detector signal output at a particular point in time Once the constant values are determined, the correlations can be used to determine future propane, butane, and pentane contents of crude samples without having to analyze each sample specifically for each target component.

Figure 4:
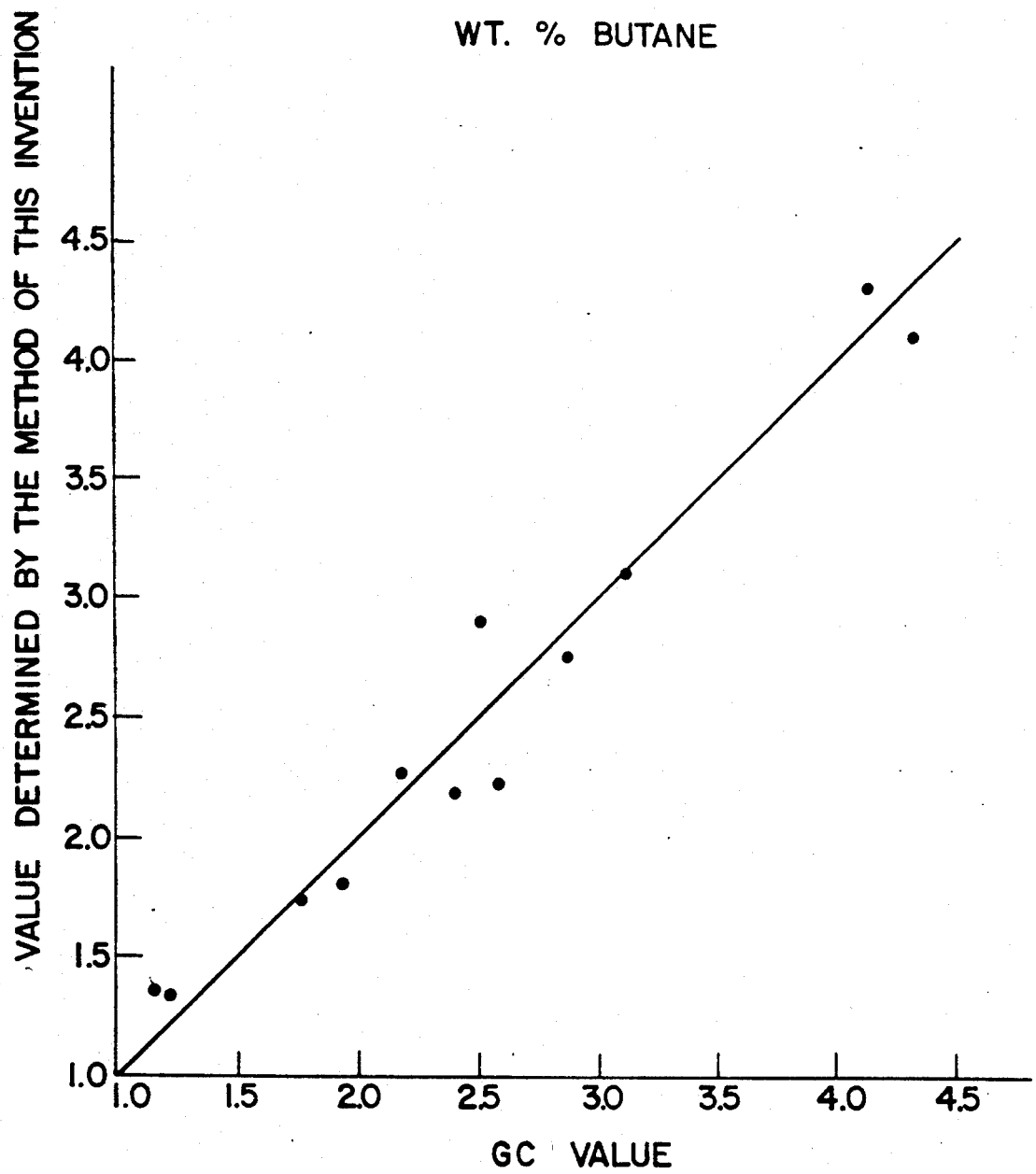
FIG. 4 depicts a plot of the correlation determined in accordance with the invention after a regression analysis program was carried out on samples having known butane contents.

FIG. 4 depicts a plot of the butane wt % content values generated by the correlation determined in accordance with the method of the invention versus butane values measured by using conventional chromatographic techniques. This plot shows the accuracy of butane content determinations in accordance with the invention versus conventional laboratory methods.

EXAMPLE 3

The apparatus and method of the present invention was employed to determine the RVP of the same 16 samples as set out in Example 2. Specifically, the same invention method as described in Example 2 was carried out for each sample.

Figure 5:
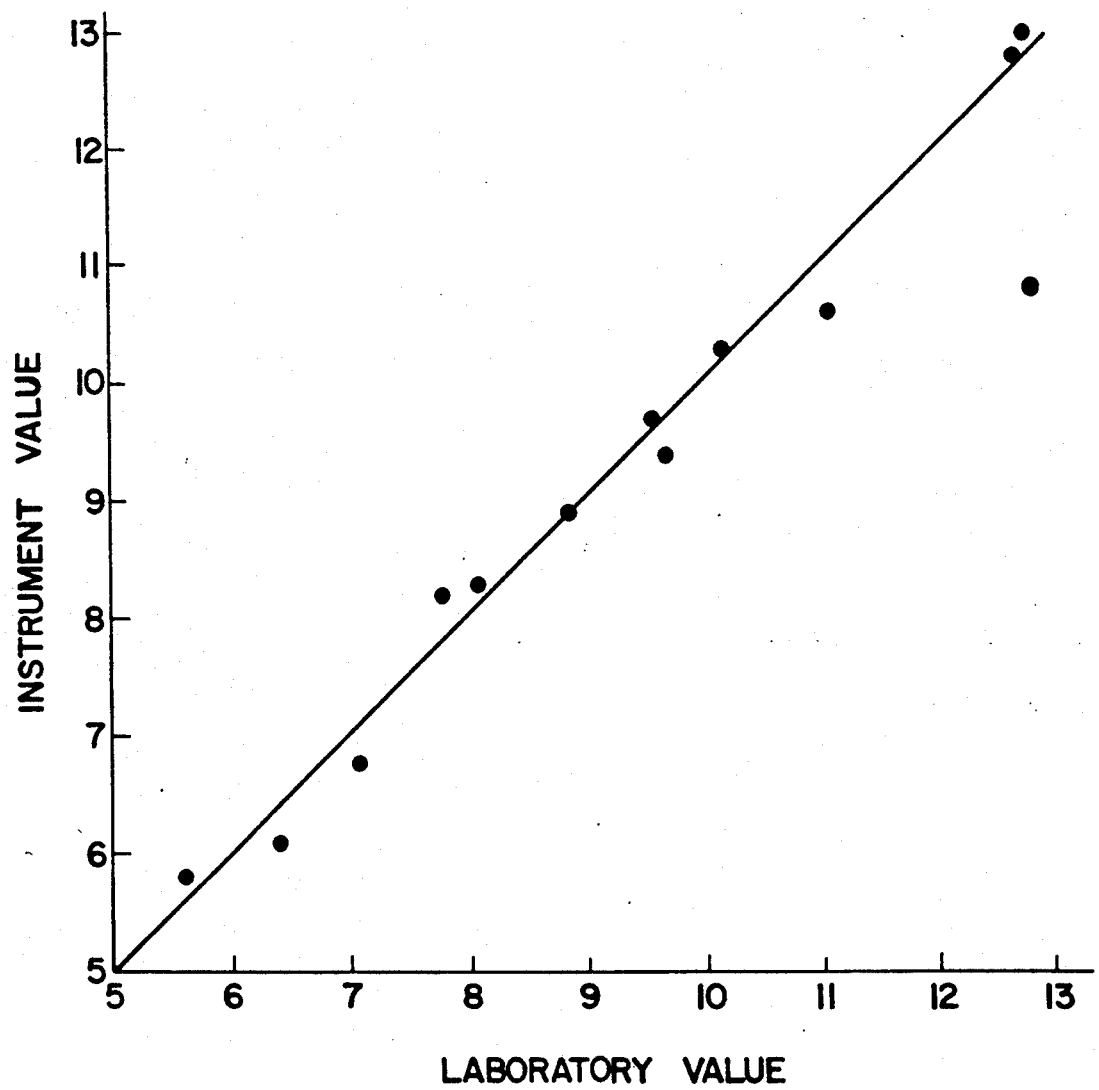
FIG. 5 depicts a plot of a correlation determined in accordance with the invention after a regression analysis program was carried out on samples having known RVP's.

For each sample analyzed in accordance with the method of the invention a comparison sample was taken and cooled to 40° F. The comparison samples were then analyzed at a laboratory using the ASTM D-323 test method. FIG. 5 plots the value of RVP determined by the correlation derived in accordance with the present invention, "instrument value" versus the laboratory value for 13 of the samples.

Note that since the laboratory value determined in accordance with the ASTM D-323 test method has a tolerance of only ±0.3 units the invention versus instrument agreement is satisfactory. The instrument detector reading was used to calculate RVP in accordance with the following formula:

$$RVP = a \frac{1}{T - A} \text{ (peak reading)} + b$$

where:
a = 282.7
T = stripper temperature, °K.
b = 2.33
A = temperature correction constant = 243

In the above equation, the temperature correction constant A was determined by varying the temperature of a particular sample from 40° F. to 110° F. The value of the constant was then set such that the above equation would yield a constant value for different temperatures where b=o in the equation. Constants a and b were determined by analysis in accordance with the present invention by using the following samples:

| Sample | Temp., °K. | RVP |
|---|---|---|
| Clear Creek | 279 | 9.6 |
| East Painter | 289 | 10.2 |
| Painter Central | 284 | 8.1 |
| Divide Sour | 287 | 5.6 |
| Glasscook | 273 | 9.7 |

What is claimed is:

1. A method for measuring the concentration of at least one target component present in a liquid comprising the steps of:
   (a) obtaining a sample of said liquid having a predetermined volume;
   (b) commingling said sample with a diluent to form a sample-diluent mixture;
   (c) passing said mixture to a stripping zone;
   (d) stripping said target component from said mixture with a stripping gas at a predetermined stripping gas flow rate and predetermined stripping conditions;
   (e) passing said stripped target component to a detection zone at a predetermined rate;
   (f) generating a signal in said detection zone responsive to the quantity of said target component; and
   (g) utilizing a chemometric model to correlate said signal to said concentration and determining said concentration of said target component in said liquid.

2. The method of claim 1 wherein said liquid is a hydrocarbon.

3. The method of claim 2 wherein said diluent comprises cumene.

4. The method of claim 2 wherein said target component is selected from the group consisting of propane, butane, and pentane.

5. The method of claim 4 wherein said target component is butane.

6. The method of claim 5 wherein said diluent is present in an amount ranging from about 30 to about 50 volumes diluent per volume sample.

7. The method of claim 1 wherein said diluent is present in an amount ranging from about 0.5 to about 150 volumes diluent per volume sample.

8. The method of claim 7 wherein said diluent is present in an amount ranging from about 20 to about 100 volumes diluent per volume sample.

9. The method of claim 7 wherein said diluent is present in an amount ranging from about 30 to about 50 volumes diluent per volume sample.

10. The method of claim 1 which comprises stripping at least two target components from said mixture and determining the concentration of said target components in said liquid.

11. A method for determining the Reid Vapor Pressure of a hydrocarbon liquid comprising target components comprising the steps of:
   (a) obtaining a sample of said liquid having a predetermined volume;
   (b) commingling said sample with a diluent to form a sample diluent mixture;
   (c) passing said mixture to a stripping zone;
   (d) stripping said target components from said mixture with a stripping gas at a predetermined stripping gas flow rate and predetermined stripping conditions;
   (e) passing said stripped target components to a detection zone at a predetermined rate;
   (f) generating a signal in said detection zone responsive to the quantity of each target component;
   (g) utilizing a chemometric model to correlate said signal to said Reid Vapor Pressure and determining said Reid Vapor Pressure of said liquid.

* * * * *